United States Patent
Kim

(10) Patent No.: US 9,962,320 B2
(45) Date of Patent: May 8, 2018

(54) COMPOSITION OF HYDROGEL SOAP, HYDROGEL SOAP AND PREPARING METHOD THEREOF

(71) Applicant: JT CO., LTD, Gyeonggi-do (KR)

(72) Inventor: Jong Thek Kim, Incheon (KR)

(73) Assignee: JT CO., LTD., Siheung-si, Gyeonggi-do (KR)

( * ) Notice: Subject to any disclaimer, the term of this patent is extended or adjusted under 35 U.S.C. 154(b) by 0 days. days.

(21) Appl. No.: 14/774,757

(22) PCT Filed: Sep. 27, 2013

(86) PCT No.: PCT/KR2013/008665
§ 371 (c)(1),
(2) Date: Sep. 11, 2015

(87) PCT Pub. No.: WO2014/185597
PCT Pub. Date: Nov. 20, 2014

(65) Prior Publication Data
US 2016/0022552 A1    Jan. 28, 2016

(30) Foreign Application Priority Data

May 16, 2013 (KR) .......................... 10-2013-0055435

(51) Int. Cl.
| | | |
|---|---|---|
| C11D 7/50 | (2006.01) | |
| B41J 2/165 | (2006.01) | |
| A61K 8/04 | (2006.01) | |
| C11D 3/04 | (2006.01) | |
| C11D 3/20 | (2006.01) | |
| C11D 3/22 | (2006.01) | |
| A61K 8/34 | (2006.01) | |
| A61K 8/41 | (2006.01) | |
| A61K 8/60 | (2006.01) | |
| A61Q 19/10 | (2006.01) | |
| A61K 8/42 | (2006.01) | |
| A61K 8/44 | (2006.01) | |
| A61K 8/73 | (2006.01) | |
| A61K 8/20 | (2006.01) | |
| C11D 1/10 | (2006.01) | |
| C11D 1/14 | (2006.01) | |
| C11D 1/52 | (2006.01) | |
| C11D 1/90 | (2006.01) | |

(52) U.S. Cl.
CPC .............. *A61K 8/042* (2013.01); *A61K 8/20* (2013.01); *A61K 8/345* (2013.01); *A61K 8/41* (2013.01); *A61K 8/416* (2013.01); *A61K 8/42* (2013.01); *A61K 8/44* (2013.01); *A61K 8/442* (2013.01); *A61K 8/60* (2013.01); *A61K 8/73* (2013.01); *A61Q 19/10* (2013.01); *C11D 3/046* (2013.01); *C11D 3/2041* (2013.01); *C11D 3/222* (2013.01); *C11D 3/225* (2013.01); *A61K 2800/5922* (2013.01); *C11D 1/10* (2013.01); *C11D 1/146* (2013.01); *C11D 1/523* (2013.01); *C11D 1/90* (2013.01)

(58) Field of Classification Search
CPC .................................................... A61K 8/042
USPC ........................................................ 510/158
See application file for complete search history.

(56) References Cited

U.S. PATENT DOCUMENTS

| | | | |
|---|---|---|---|
| 6,780,825 B2 * | 8/2004 | Piterski ................. | A61K 8/442 424/70.11 |
| 6,838,420 B2 | 1/2005 | Sachdev | |
| 2002/0077256 A1 * | 6/2002 | Niemiec ................ | A61K 8/731 510/119 |
| 2002/0177535 A1 * | 11/2002 | Piterski ................. | A61K 8/442 510/130 |
| 2003/0166480 A1 | 9/2003 | Sachdev | |
| 2005/0215443 A1 * | 9/2005 | Littau ...................... | A61K 8/03 510/130 |
| 2009/0312215 A1 * | 12/2009 | Glenn .................... | A47L 13/10 510/158 |
| 2010/0055055 A1 * | 3/2010 | Albeck ................. | A61K 31/555 424/59 |
| 2013/0029932 A1 | 1/2013 | Kachi et al. | |
| 2016/0022552 A1 * | 1/2016 | Kim ....................... | A61K 8/416 510/158 |

FOREIGN PATENT DOCUMENTS

| | | |
|---|---|---|
| KR | 10-2004-0053807 A | 6/2004 |
| KR | 10-2004-0094741 A | 11/2004 |
| KR | 10-2006-0118944 A | 11/2006 |
| KR | 10-2009-0010344 A | 1/2009 |
| KR | 1020090010344 A * | 1/2009 |
| KR | 10-2013-0028062 A | 3/2013 |

OTHER PUBLICATIONS

A machine Translation of KR 1020090010344 A.*

* cited by examiner

*Primary Examiner* — Nicole M Buie-Hatcher
*Assistant Examiner* — M. Reza Asdjodi
(74) *Attorney, Agent, or Firm* — Rabin & Berdo, P.C.

(57) ABSTRACT

Composition of a hydrogel soap, a hydrogel soap, and a method of preparing the same. The hydrogel soap represents detergency or moisturizing power superior to that of a general soap and has weak acidity or neutral-pH (pH 5.0 to pH 7.0), so that the skin irritation is mitigated and superior formability is represented.

6 Claims, No Drawings

COMPOSITION OF HYDROGEL SOAP, HYDROGEL SOAP AND PREPARING METHOD THEREOF

BACKGROUND OF THE INVENTION

1. Field of the Invention

The present invention relates to a composition of a hydrogel soap, a hydrogel soap, and a method of effectively preparing the same.

2. Description of the Related Art

In general, soaps are classified into soft or hard solid soaps including CP, MP, and HP soaps and liquid soaps. The general soaps are prepared by dissolving fatty acid or vegetable oil, performing a saponification reaction by using sodium hydroxide or potassium hydroxide, and mixing proper additives with the resultant. The soaps represent strong alkaline properties of pH 8.0. Accordingly, if a large amount of moisturizing ingredients are not contained in the soaps, the skin of a user may become pulled, and skin irritation may occur.

Recently, as the interest in beauty is increased regardless of age and sex, the tendency of using facial cleansers and/or body cleansers instead of soaps when a user washes up or takes a bath is increased. Since the products have the form of a liquid, the products additionally require storage containers. Accordingly, the manufacturing cost and/or the price of the product are more expensive that those of a general soap.

Although a jelly soap based on gelatin (disclosed in Korea Patent Publication No. 2004-53807) has a foaming power and detergency, the jelly soap may be easily softened. In addition, when the jelly soap is exposed to water, stickiness may significantly remain due to the characteristic of the jelly soap. Accordingly, if a user does not sufficiently rinse the jelly soap by water, residues of the soap may remain. In addition, a hydrogel soap (disclosed in Korea Patent Publication No. 2009-10344) may represent alkalinity having slightly higher acidity and may have no elasticity.

Therefore, there are increased demands for a novel soap composition and a novel soap in which the soap must have neutral-pH or weak acidity in order to minimize skin irritation and reduce an amount of introduced humectants, must improve detergency, which is the original object of the soap, can be prepared in various shapes, and can represent superior formability.

SUMMARY OF THE INVENTION

Therefore, the inventors of the present invention have completed the present invention by using the optimal compositions and the optimal composition ratios for a soap representing superior detergency, superior moisturizing power, and the optimal pH, and especially representing superior formability after putting in a great deal of effort. In other words, the present invention provides a composition of a hydrogel soap, a method of preparing the hydrogel soap, and the hydrogel soap prepared through the method.

In order to accomplish the above object, according to one aspect of the present invention, there is provided a composition of a hydrogel soap including 1 to 10% by weight of a gelling agent, 5 to 35% by weight of a surfactant, 2 to 30% by weight of a humectant, 0.05 to 2% by weight of a curing agent, and 30 to 80% by weight of purified water.

According to another aspect of the present invention, there is provided a method of preparing a composition of a hydrogel soap. The method includes preparing a mixture by adding a gelling agent, a humectant, and a curing agent into purified water, heating a resultant at a temperature in the range of 40° C. to ° C., and stirring and dissolving the resultant, preparing a hydrogel soap solution by adding a surfactant into the mixture and stirring a resultant, and cooling the hydrogel soap solution at a temperature in a range of 0° C. to 45° C.

In addition, the hydrogel soap is prepared by using the composition of the hydrogel soap described above. The hydrogel soap may have acidity in a range of pH 5.0 to pH 7.0, and viscosity in a range of 1,800 cps to 9,500 cps at a temperature in a range of 35° C. to 55° C. when the viscosity is measured a Brookfield viscometer.

As described above, the present invention represents detergency or moisturizing power superior to that of a general soap and has weak acidity or the acidity of neutral-pH (pH 5.0 to pH 7.0), so that the skin irrigation can be mitigated and variously shaped soaps can be formed if a proper temperature is maintained.

DETAILED DESCRIPTION OF THE INVENTION

Hereinafter, the present invention will be described in more detail.

Compositions of a hydrogel soap according to the present invention may include a gelling agent, a surfactant, a humectant, a curing agent, and purified water. In more detail, the composition of the hydrogel soap may include 1 to 10% by weight of a gelling agent, 5 to 35% by weight of the surfactant, 2 to 30% by weight of humectant, 0.05 to 2% by weight of a curing agent, and 30 to 80% by weight of purified water.

The gelling agent, which is one of the compositions according to the present invention, serves as a support member or a support of a soap according to the present invention. The gelling agent may include at least one selected from the group consisting of a guar gum, an agar, a carrageenan, a sodium alginate, a locust bean gum, a xanthan gum, an arabic gum, a gellan gum, a carboxy methyl celluose (CMC), a *ceratonia siliqua* gum, and a konjac, or may be mixed with another proper gelling agent according to the uses thereof. In addition, an amount of the used gelling agent is in the range of 1 to 10% by weight, preferably, 1 to 5% by weight, and, more preferably, 1 to 3% by weight based on the whole weight of the hydrogel soap. In this case, if less than 1% by weight of the gelling agent is used, the soap composition is not sufficiently changed to a gel, the inferior moisturizing power and foaming power may be represented. If the amount of the used gelling agent exceeds 10% by weight, the detergency may be degraded. Accordingly, it is advantageous that the gelling agent is used in the above range.

The surfactant, which is one of the compositions according to the present invention, serves as detergent in the present invention. The surfactant may include at least one of an alkyl sulfate surfactant, an alkyl ether sulfate surfactant, an amino acid-induced surfactant, a sulfosuccinate surfactant, an alkanoylamide surfactant, an alkyl betaine surfactant, amphodiacetate surfactant, and a natural surfactant.

In addition, preferably, the surfactant may include two or three kinds of mixtures obtained by mixing at least one selected from the group consisting of an alkyl ether sulfate surfactant and a sulfosuccinate surfactant, which are effective in preventing and improving skin allergy because the surfactants represent superior skin moisturizing power, superior antimicrobial functions, and superior detergency, with an amino acid-induced surfactant serving as an anionic surfactant and a main element of collagen for detergency and foam stability. Further, more preferably, the surfactant may additionally include an alkyl betaine surfactant together with the amino acid-induced surfactant, the alkyl ether sulfate surfactant and/or the sulfosuccinate surfactant for the use thereof. The alkyl betaine surfactant is a surfactant which sufficiently generates foams and is mild with respect to a skin. Since the alkyl betaine surfactant represents a superior characteristic to form viscosity and has a cationic property, antimicrobial activity and the effects of a conditioner can be obtained.

In addition, the alkyl sulfate surfactant may include at least one selected from the group consisting of ammonium lauryl sulfate and TEA lauryl sulfate, and the alkyl ether sulfate surfactant may include at least one selected from the group consisting of sodium laureth sulfate and ammonium laureth sulfate. In addition, the amino acid-induced surfactant may include at least one selected from the group consisting of TEA cocoyl glutamate, disodium lauroyl glutamate, sodium lauroyl glutamate, sodium cocoyl alaninate, and sodium cocoyl apple amino acids, and the sulfosuccinate surfactant may include at least one selected from the group consisting of disodium laureth sulfosuccinate and disodium lauroyl sulfosuccinate. In addition, the alkanoyl-amide surfactant may include at least one selected from the group consisting of lauramide DEA, cocamide MEA, and cocamide DEA. The alkyl betaine surfactant is a surfactant to hardly represent skin irritation and may include at least one selected from the group consisting of lauramidopropyl betaine, cocamidopropyl betaine, and babassuamidopropyl betaine. The amphodiacetate surfactant may include at least one selected from the group consisting of disodium coco-amphodiacetate and disodium lauroamphodiacetate. In addition, the natural surfactant may include at least one selected from the group consisting of potassium olivate, potassium olivoyl PCA and decyl glucocide.

According to the present invention, an amount of a used surfactant is in the range of 5 to 35% by weight, preferably, 10 to 30% by weight, and more preferably, 10 to 25% by weight based on the whole weight of the hydrogel soap. In addition, if the content of the gelling agent is less than 5% by weight, the inferior foaming power may be represented. If the content of the gelling agent exceeds 35% by weight, superior foaming power may be represented, but an amount of humectant and an amount of gel solution are relatively reduced, so that the hardness, the skin irritation, and the detergency of the gel may be degraded.

The humectant, which is one of compositions according to the present invention, is used to additionally provide the moisturizing effect to the skin, and may include at least one selected from the group consisting of glycerin, propylene glycol, butylene glycol, sorbitol, hyaluonic acid, polyglutamic acid, and sodium PCA. In addition, an amount of a used humectant is in the range of 2 to 30% by weight, preferably, 5 to 28% by weight, and more preferably, 10 to 25% by weight based on the whole weight of the hydrogel soap. In addition, if the amount of the used humectant is less than 2% by weight, the skin moisturizing power may be degraded. If the amount of the used humectant exceeds 30% by weight, an amount of a surfactant is relatively decreased, so that foams may not be sufficiently generated or moisturizing power may not be sufficiently formed.

The curing agent, which is one of the composites according to the present invention, may adjust a curing rate in the present invention, and may include at least one selected from the group consisting of calcium chloride, potassium chloride, and calcium hydroxide. In addition, an amount of a used curing agent is in the range of 0.05 to 2% by weight, preferably, 0.1 to 1.5% by weight, and more preferably, 0.1 to 1% by weight based on the whole weight of the hydrogel soap. In addition, if an amount of a used curing agent is less than 0.05% by weight, an extremely small amount of the curing agent is used, and the curing time is prolonged. If the amount of the used curing agent exceeds 2% by weight, an excessive amount of the curing gent is used, so that coagulation is rapidly proceeded to degrade formability. Accordingly, it is advantageous that the curing agent is used in the above range.

In addition, the purified water, which is one of the compositions according to the present invention, serves a solvent. An amount of used purified water is determined depending on an amount of other compositions that are used. Preferably, the content of purified water may be in the range of 30 to 80% by weight based on the whole weight of the hydrogel soap.

The compositions of the hydrogel soap according to the present invention may further include additives in addition to the gelling agent, the surfactant, the humectant, the curing agent, and the purified water that have been described above. The additives may include at least one selected from the group consisting of flavoring agents, coloring agents, preservatives, and sequestering agents. In addition, regarding a proper amount of used flavoring agents, the coloring agents, the preservatives, and the sequestering agents, 0.05 to 2 parts by weight of the flavoring agents, 0.01 to 1 parts by weight of the coloring agent, 0.001 to 0.5 parts by weight of the preservative and 0.001 to 0.5 parts by weight of the sequestering agent are preferably used based on 100 parts by weight of the compositions including the gelling agent, the surfactant, the humectant, curing agent, and the purified water.

Hereinafter, a method of preparing the hydrogel soap according to the present invention will be described.

According to the present invention, the hydrogel soap was prepared through processes including a step of preparing a mixture by adding the gelling agent, the humectant, and the curing agent into the purified water, raising the temperature to a value in the range of 40° C. to 90° C., and stirring and dissolving the resultant, a step of preparing a hydrogel soap solution by adding the surfactant into the mixture and stirring the resultant, and a step of cooling the hydrogel soap solution at the temperature of 0° C. to 45° C.

In addition, the preparing method may further include a step of introducing at least one selected from the group consisting of flavoring agents, coloring agents, preservatives, and sequestering agents into the cooled hydrogel soap solution and stirring the resultant.

The temperature is raised to the value in the 40° C. to 90° C., preferably, 40° C. to 70° C. when the mixture is prepared, so that the compositions of the mixture can be easily stirred and dissolved, and can be uniformly mixed with each other. If the composites of the mixture is stirred and dissolved at the temperature of less than 40° C., the composites may not be sufficiently dissolved. If the temperature exceeds 90° C., the property of the effective components such as hermectants may be changed, and the gel strength may be degraded. Accordingly, it is advantageous that the compositions of the mixture are heated to the temperature in the above range and stirred and dissolved.

The hydrogel soap prepared through the method based on the above compositions of the hydrogel soap has the acidity of pH 5.0 to pH 7.0, preferably, pH 5.5 to pH 7.0, which hardly irritates a skin of the user, can represent superior foaming power, and provide superior detergency to the user.

In addition, the hydrogel soap according to the present invention may have the viscosity of 1,800 cps to 9,500 cps at the temperature of 35° C. to 55° C. when the viscosity of the hydrogel soap is measured by a Brookfield viscometer. Further, the hydrogel soap according to the present invention may have the hardness of 500 dyne/cm² to 700 dyne/cm², preferably, 550 dyne/cm² to 680 dyne/cm². In addition, the hydrogel soap according to the present invention represents the sol-gel transition temperature of 28° C. to 34° C., preferably, 28° C. to 32° C.

Hereinafter, the present invention will be described in more detail according to embodiments, but the scope of the present invention is not limited to following embodiments.

EMBODIMENT

Embodiment 1: Preparation of Hydrogel Soap

After putting purified water into a 1 L-beaker, carageenan and a xantangum serving as the gelling agents were mixed with each other at a weight ratio of 1:1 to make a mixed solution. Glycerin serving as the humectant and calcium chloride serving as the curing agent were added into the mixed solution, heated to the temperature of 50° C., and stirred and dissolved for 15 minutes to prepare a mixture.

Thereafter, a hydrogel soap solution including 2.5% by weight of the gelling agent, 25% by weight of the surfactant, 10% by weight of the humectant, 1% by weight of the curing agent, and 61.5% by weight of the purified water was prepared by adding lauramidopropyl betaine serving as the surfactant into the mixture and stirring the resultant.

Subsequently, based on 100 parts by weight of the hydrogel soap solution, 0.3 parts by weight of the flavoring agent, 0.1 parts by weight of the coloring agent, 0.4 parts by weight of the preservative, and 0.02 parts by weight of the sequestering agent were introduced into the hydrogel soap solution and then stirred to prepare the hydrogel soap.

Next, the hydrogel soap solution was left at the temperature of 25° C. or less and cooled.

Embodiments 2 to 5 and Comparative Example 1

The hydrogel soap was prepared in the same manner as that of the embodiment 1 and Embodiments 2 to 5, and comparative example 1 were made by preparing the hydrogel soap with the composition shown in following table 1.

TABLE 1

| Division (% by weight) | Embodiment 1 | Embodiment 2 | Embodiment 3 | Embodiment 4 | Embodiment 5 | Comparative Example 1 | Comparative Example 2 | Comparative Example 3 |
|---|---|---|---|---|---|---|---|---|
| purified water | 61.5 | 51.5 | 59 | 54 | 69 | 63.5 | 50.5 | 49 |
| gelling agent | 2.5 | 2.5 | 5 | 10 | 5 | 0.5 | 2.5 | 15 |
| surfactant | 25 | 20 | 25 | 25 | 15 | 25 | 40 | 25 |
| humectant | 10 | 25 | 10 | 10 | 10 | 10 | 10 | 10 |
| curing agent | 1 | 1 | 1 | 1 | 1 | 1 | 1 | 1 |
| total amount | 100% by weight (parts by weight) | | | | | | | |
| flavoring agent | 0.3 parts by weight | | | | | | | |
| coloring agent | 0.1 parts by weight | | | | | | | |
| preservative | 0.4 parts by weight | | | | | | | |
| sequestering agent | 0.02 parts by weight | | | | | | | |

Experimental Example 1: Experiment of Measuring Properties

The gel formation state, the elasticity, the foaming power, the detergency, the degree of skin irritation, and the moisturizing power of the hydrogel soap prepared in the embodiments 1 and 2 and comparative examples 1 to 5 were measured and the measurement results are shown in table 2.

The gel formation state of the hydrogel soap was confirmed by the naked eyes, the pH of the hydrogel soap was measured by a pH meter (Model: PC-700, Manufacturer: EUTECH, Singapore), and the elasticity of the hydrogel soap was measured by a hardness meter (Model: L CR-200D, 2 pin, 120 mm/min, Manufacturer: SUN SCIENTIFIC CO. LTD). The moisturizing power was measured by a moisture meter (Model: MOISTURE CHECKER MY-3088, Manufacturer: SCALAR corp.). In addition, the foaming power, the detergency, and the degree of the skin irritation were measured by a self-quality evaluation group having 10 selected members.

TABLE 2

| Division (% by weight) | Embodiment 1 | Embodiment 2 | Embodiment 3 | Embodiment 4 | Embodiment 5 | Comparative Example 1 | Comparative Example 2 | Comparative Example 3 |
|---|---|---|---|---|---|---|---|---|
| gel formation state | ● | ● | ● | ● | ● | X | ▲ | ● |
| elasticity | ● | ● | ● | ● | ● | X | ▲ | ▲ |
| foaming power | ● | ● | ● | ● | ▲ | ▲ | ● | ▲ |

TABLE 2-continued

| Division (% by weight) | Embodiment 1 | Embodiment 2 | Embodiment 3 | Embodiment 4 | Embodiment 5 | Comparative Example 1 | Comparative Example 2 | Comparative Example 3 |
|---|---|---|---|---|---|---|---|---|
| detergency | ● | ● | ▲ | ▲ | ▲ | ▲ | ▲ | X |
| Degree of skin irritation | ● | ● | ● | ● | ● | ▲ | X | ▲ |
| moisturizing power | ● | ● | ● | ● | ● | ▲ | ● | ● |
| pH | 5.51 | 5.72 | 5.92 | 6.02 | 5.82 | 6.70 | 5.42 | 6.32 |

●: good, ▲: moderate, X: bad or not formed.

Regarding the experimental result shown in table 2, it can be recognized that superior gel formation, superior elasticity, superior foaming power, superior detergency, the low degree of skin irritation, and superior moisturizing power can be wholly represented in embodiments 1 to 5. However, in comparative example 1 in which the gelling agent is used in the content of 1% by weight or less, gel is not formed, so that the elasticity is hardly represented, and inferior foaming power is represented.

Further, comparative example 2 in which the content of the surfactant exceeds 40% by weight shows results inferior to those of embodiments 1 to 5 in a gel formation degree, elasticity, and the degree of skin irritation.

In comparative example 3 in which the content of the used gelling agent is 15% by weight more than 10% by weight, inferior detergency is represented.

Experimental Example 2: Experiment of Measuring Viscosity

The viscosity of the hydrogel soap prepared in Embodiment 1 was measured in a water bath (C-WBE, CHANG SHIN CO.) at each temperature of 55° C. to 20° C. while each temperature of 55° C. a gel formation degree, elasticity, and the degree of skin irritation to 20° C. is being maintained for 15 minutes.

TABLE 3

| Temperature (° C.) | Viscosity (cps) |
|---|---|
| 55 | 1,830 |
| 50 | 3,920 |
| 45 | 5,220 |
| 40 | 6,850 |
| 35 | 9,380 |
| 30 | 24,060 |
| 25 | 55,000 |
| 20 | 80,000 or more |

The experimental result of table 3 shows that the viscosity of the hydrogel soap is 1,830 cps at the temperature of 55° C. increased as the temperature is lowered, and 9,380 cps at 35° C. In addition, the viscosity of the hydrogel soap is rapidly increased to 24,060 cps or more from the temperature of 30° C. Therefore, the sol-gel transition temperature of the hydrogel soap according to the present invention is in the range of 28° C. to 34° C., preferably, 28° C. to 32° C.

Experimental Example 3: Experiment of Measuring Hardness

After the hydrogel soaps prepared according to the embodiments and the comparative examples were subject to an aging period of one day, the gel hardness of each hydrogel soap was measured, and the measurement results are shown in table 4.

TABLE 4

| Division | Hardness (dyne/cm$^2$) | Hardness after Friction (dyne/cm$^2$) |
|---|---|---|
| Embodiment 1 | 582 | 580 |
| Embodiment 2 | 580 | 576 |
| Embodiment 3 | 630 | 628 |
| Embodiment 4 | 652 | 650 |
| Embodiment 5 | 550 | 542 |
| Comparative Example 1 | — | — |
| Comparative Example 2 | 430 | 412 |

The experimental result of table 4 shows that the proper hardness of 500 to 700 is represented in embodiments 1 to 5. However, since gel is not formed in the comparative example 1, the hardness measurement is impossible. In addition, excessively lower hardness is represented in comparative example 2.

Experimental Example 4: Measurement of Moisture in Skin after Washing Up Using Hydrogel Soap An amount of moisture was measured according to skin types before and after the use of the hydrogel soap (Model: MY-308, Manufacture: SCALAR corp. MOISTURE CHECKER) and the measurement results are shown in following table 5.

A moisturizing degree was measured with respect to each of five persons having dry skins and five persons having oily skins before and after the use of the hydrogel soap, and an average moisturizing degree was calculated.

TABLE 5

| Skin type | Before Use | After Use | | | |
|---|---|---|---|---|---|
| | | General Soap | Cosmetic Soap (Facial Cleanser) | Hydrogel soap in Embodiment 1 | Facial Cream |
| Dry Skin | 31.7 | 31.1 | 33.4 | 33.9 | 34 |
| Oily Skin | 33.1 | 30.9 | 33.7 | 36.4 | 36.6 |

According to the measurement results, when a user washes up by using a general soap for a face (which is a product obtained from saponification reaction of fatty acid), the lowest moisture is represented, so that a user feels that the skin of the user is pulled. In addition, when the user washes up by using a facial cleanser which is most extensively used in a market, the facial cleanser represents superior foaming power or superior detergency. However, most facial cleansers sting the eyes of the user when portions of the facial cleansers are introduced into the eyes of the user.

Meanwhile, after washing up by using the hydrogel soap prepared according to Embodiment 1, a user feels a moisturizing degree represented in a skin when the user has applied facial cream to the face of the user.

Embodiments 6 to 9 and Experimental Example 5: Experiment of Measuring Gel Formation Degree According to Types of Surfactants The hydrogel soap was prepared in the same manner as that of Embodiment 1, a gelling agent, which was obtained by mixing a xanthan gum, a carrageenan, and an agar at the weight ratio of 2:1:1, was used, and embodiments 6 to 9 are made by allowing the surfactant to have the compositions shown in table 6.

Next, a gel formation degree was formed with respect to each of hydrogel soaps of embodiments 6 to 9 prepared according to the types of the surfactant, and the measurement result is shown in table 6. In addition, the gel formation degree was relatively evaluated based on five points by a self-quality evaluation group, in which points "1", "2", "3", "4", and "5" refer to "very bad", "bad", "normal", "good", and "very good", respectively.

TABLE 6

| Division (% by weight) | | | Embodiment 6 | Embodimen7 | Embodimen8 | Embodimen9 |
|---|---|---|---|---|---|---|
| purified water | | | 63 | 62.5 | 60.5 | 38.5 |
| gelling agent | | | 3.5 | 3.5 | 3.5 | 3.5 |
| Surfactant | Alkyl betaine | lauramido propyl betaine | 22 | — | — | 22 |
| | Amino acid derivatives | TEAcocoyl glutamate | 0.5 | 22 | 5 | 22 |
| | Alkyl Sulfate | Ammonium lauryl sulfate | — | — | 22 | — |
| | alkanoyl-amide | Lauramide DEA | — | 3 | — | 3 |
| Humectants | | | 10 | 10 | 10 | 10 |
| Curing agent | | | 1 | 1 | 1 | 1 |
| Total amount | | | 100% by weight (parts by weight) | | | |
| Flavoring agent | | | 0.3 parts by weight | | | |
| Coloring agent | | | 0.1 parts by weight | | | |
| Preservative | | | 0.4 parts by weight | | | |
| Sequestering agent | | | 0.02 parts by weight | | | |
| Gel Formation Degree | | | 5.0 | 4.7 | 2.0 | 2.9 |

As shown in table 6, the high gel formation degree is represented in embodiment 6 employing alkyl betaine and amino acid derivatives for surfactants and embodiment 7 employing amino acid derivatives and alkanoylamide for surfactants. Accordingly, when the surfactant is mixed for use in order to prepare a hydrogel soap representing the high gel formation degree, it is advantageous that an alkyl betaine surfactant and an amino acid-induced surfactant are mixed together or the amino acid-induced surfactant and an alkanoylamide surfactant are mixed together.

What is claimed is:

1. A composition of a hydrogel soap, the composition consisting of:
   1 to 10% by weight of a gelling agent;
   20 to 25% by weight of a surfactant;
   10 to 25% by weight of a humectant;
   0.05 to 2% by weight of a curing agent;
   30 to 80% by weight of purified water; and
   0.05 to 2 parts by weight of a flavoring agent, 0.01 to 1 parts by weight of a coloring agent, 0.001 to 0.5 parts by weight of a preservative, and 0.001 to 0.5 parts by weight of a sequestering agent, based on 100 parts by weight of the composition consisting of the gelling agent, the surfactant, the humectant, the curing agent, and the purified water, wherein,
   the gelling agent comprises at least two selected from the group consisting of an agar, a carrageenan, a sodium alginate, a locust bean gum, a xanthan gum, an arabic gum, a gellan gum, a carboxymethylcelluose (CMC), a *ceratonia siliqua* gum, and a konjac,
   the surfactant comprises at least two selected from the group consisting of an alkyl betaine surfactant, an amino acid-induced surfactant, an alkyl ether sulfate surfactant, and a sulfosuccinate surfactant,
   the alkyl betaine surfactant comprises at least one selected from the group consisting of lauramidopropyl betaine, cocamidopropyl betaine and babassuamidopropyl betaine,
   the amino acid-induced surfactant comprises at least one selected from the group consisting of TEA cocoyl glutamate, disodium lauroyl glutamate, sodium lauroyl glutamate, sodium cocoyl alaninate, and sodium cocoyl apple amino acids,
   the alkyl ether sulfate surfactant comprises at least one selected from the group consisting of sodium laureth sulfate and ammonium laureth sulfate, and
   the sulfosuccinate surfactant comprises at least one selected from the group consisting of disodium laureth sulfosuccinate and disodium lauroyl sulfosuccinate.

2. The composition of claim 1, wherein the humectant comprises at least one selected from the group consisting of glycerin, propylene glycol, butylene glycol, sorbitol, hyaluonic acid, polyglutamic acid, and sodium PCA.

3. The composition of claim 1, wherein the curing agent comprises at least one selected from the group consisting of calcium chloride, potassium chloride, and calcium hydroxide.

4. The hydrogel soap of claim 1, wherein the hydrogel soap has acidity in a range of pH 5.0 to pH 7.0, and hardness in a range of 500 dyne/cm$^2$ to 700 dyne/cm$^2$.

5. The hydrogel soap of claim 1, wherein the hydrogel soap has a sol-gel transition temperature in a range of 28 to 34.

6. A composition of a hydrogel soap, consisting of:
1 to 10% by weight of a gelling agent;
10 to 30% by weight of a surfactant;
2 to 30% by weight of a humectant;
0.05 to 2% by weight of a curing agent;
30 to 80% by weight of purified water; and
based on 100 parts by weight of the composition consisting of the gelling agent, the surfactant, the humectant, the curing agent, and the purified water,
0.05 to 2 parts by weight of a flavoring agent,
0.01 to 1 parts by weight of a coloring agent,
0.001 to 0.5 parts by weight of a preservative, and
0.001 to 0.5 parts by weight of a sequestering agent, wherein, the gelling agent comprises at least two selected from the group consisting of an agar, a carrageenan, a sodium alginate, a locust bean gum, a xanthan gum, an arabic gum, a gellan gum, a carboxymethylcelluose (CMC), a *ceratonia siliqua* gum, and a konjac, the surfactant comprises at least two selected from the group consisting of an alkyl betaine surfactant, an amino acid-induced surfactant, an alkyl ether sulfate surfactant, and a sulfosuccinate surfactant, the humectant comprises at least one selected from the group consisting of glycerin, propylene glycol, butylene glycol, sorbitol, hyaluonic acid, polyglutamic acid, and sodium PCA, and the curing agent comprises at least one selected from the group consisting of calcium chloride, potassium chloride, and calcium hydroxide.

* * * * *